United States Patent
Russell et al.

(10) Patent No.: US 9,827,085 B2
(45) Date of Patent: *Nov. 28, 2017

(54) INTEGRATED EMBOLIC PROTECTION DEVICES

(71) Applicant: Emboline, Inc., Los Altos, CA (US)

(72) Inventors: Scott Russell, San Jose, CA (US); Amir Belson, Los Altos, CA (US)

(73) Assignee: Emboline, Inc., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/335,322

(22) Filed: Oct. 26, 2016

(65) Prior Publication Data
US 2017/0042659 A1 Feb. 16, 2017

Related U.S. Application Data

(63) Continuation of application No. 13/735,864, filed on Jan. 7, 2013, now Pat. No. 9,492,265.
(Continued)

(51) Int. Cl.
*A61F 2/01* (2006.01)
*A61F 2/24* (2006.01)

(52) U.S. Cl.
CPC ............ *A61F 2/013* (2013.01); *A61F 2/2427* (2013.01); *A61F 2002/011* (2013.01);
(Continued)

(58) Field of Classification Search
CPC ................ A61F 2/013; A61F 2002/016; A61F 2002/018
See application file for complete search history.

(56) References Cited

U.S. PATENT DOCUMENTS

| | | |
|---|---|---|
| 4,723,549 A | 2/1988 | Wholey et al. |
| 4,790,809 A | 12/1988 | Kuntz |

(Continued)

FOREIGN PATENT DOCUMENTS

| | | |
|---|---|---|
| CA | 2609800 A1 | 1/2007 |
| JP | H09276414 A | 10/1997 |

(Continued)

OTHER PUBLICATIONS

US 6,348,062, 02/2002, Hopkins et al. (withdrawn)
(Continued)

*Primary Examiner* — Diane Yabut
(74) *Attorney, Agent, or Firm* — Wilson Sonsini Goodrich & Rosati

(57) ABSTRACT

Embolic Protection elements are integrated with a catheter or access sheath for any catheter. A catheter shaft has an embolic filter slidably mounted on a distal portion of a catheter shaft. A proximal stop for limits proximal movement of the embolic filter, and a distal stop for limits distal movement of the embolic filter. The filter has a porous mesh material defining a collection chamber for captured emboli and has a collapsed and a deployed configuration. The filter may be collapsed by an access sheath used with the catheter. An access sheath may have a tubular main body and an embolic filter mounted on the distal portion of the tubular main body. The embolic filter may evert into the central lumen of the sheath or may be constrained on the exterior of the sheath with a larger diameter outer tube.

16 Claims, 8 Drawing Sheets

Related U.S. Application Data

(60) Provisional application No. 61/584,094, filed on Jan. 6, 2012, provisional application No. 61/738,852, filed on Dec. 18, 2012.

(52) U.S. Cl.
CPC ... *A61F 2002/015* (2013.01); *A61F 2002/016* (2013.01); *A61F 2002/018* (2013.01); *A61F 2230/008* (2013.01); *A61F 2230/0067* (2013.01); *A61F 2230/0069* (2013.01)

(56) References Cited

U.S. PATENT DOCUMENTS

| | | | |
|---|---|---|---|
| 5,108,419 | A | 4/1992 | Reger et al. |
| 5,197,485 | A | 3/1993 | Grooters |
| 5,769,816 | A | 6/1998 | Barbut et al. |
| 5,769,819 | A | 6/1998 | Schwab et al. |
| 5,797,880 | A | 8/1998 | Erskine |
| 5,800,525 | A | 9/1998 | Bachinski et al. |
| 5,807,327 | A | 9/1998 | Green et al. |
| 6,013,051 | A | 1/2000 | Nelson |
| 6,117,154 | A | 9/2000 | Barbut et al. |
| 6,139,517 | A | 10/2000 | Macoviak et al. |
| 6,152,144 | A | 11/2000 | Lesh et al. |
| 6,254,563 | B1 | 7/2001 | Macoviak et al. |
| 6,258,120 | B1 | 7/2001 | McKenzie et al. |
| 6,348,063 | B1 | 2/2002 | Yassour et al. |
| 6,355,051 | B1 | 3/2002 | Sisskind et al. |
| 6,361,545 | B1 | 3/2002 | Macoviak et al. |
| 6,371,935 | B1 | 4/2002 | Macoviak et al. |
| 6,461,370 | B1 | 10/2002 | Gray et al. |
| 6,499,487 | B1 | 12/2002 | McKenzie et al. |
| 6,537,297 | B2 | 3/2003 | Tsugita et al. |
| 6,682,543 | B2 | 1/2004 | Barbut et al. |
| 6,695,864 | B2 | 2/2004 | Macoviak et al. |
| 6,746,469 | B2 | 6/2004 | Mouw |
| 6,808,520 | B1 | 10/2004 | Fourkas et al. |
| 7,232,453 | B2 | 6/2007 | Shimon |
| 7,235,060 | B2 | 6/2007 | Kraus |
| 7,758,606 | B2 | 7/2010 | Streeter et al. |
| 7,766,932 | B2 | 8/2010 | Melzer et al. |
| 8,114,114 | B2 | 2/2012 | Belson |
| 8,308,754 | B2 | 11/2012 | Belson |
| 8,414,482 | B2 | 4/2013 | Belson |
| 8,430,904 | B2 | 4/2013 | Belson |
| 8,679,149 | B2 | 3/2014 | Belson |
| 8,728,114 | B2 | 5/2014 | Belson |
| 9,107,734 | B2 | 8/2015 | Belson |
| 9,492,265 | B2 | 11/2016 | Russell et al. |
| 2001/0044632 | A1 | 11/2001 | Daniel et al. |
| 2002/0004667 | A1 | 1/2002 | Adams et al. |
| 2002/0058964 | A1 | 5/2002 | Addis |
| 2002/0128680 | A1 | 9/2002 | Pavlovic |
| 2003/0040736 | A1 | 2/2003 | Stevens et al. |
| 2003/0100940 | A1 | 5/2003 | Yodfat |
| 2003/0171803 | A1 | 9/2003 | Shimon |
| 2004/0034380 | A1 | 2/2004 | Woolfson et al. |
| 2004/0073253 | A1 | 4/2004 | Morrill et al. |
| 2004/0138692 | A1 | 7/2004 | Phung et al. |
| 2004/0215167 | A1 | 10/2004 | Belson |
| 2004/0225354 | A1 | 11/2004 | Allen et al. |
| 2005/0010246 | A1 | 1/2005 | Streeter et al. |
| 2005/0283186 | A1 | 12/2005 | Berrada et al. |
| 2006/0287668 | A1* | 12/2006 | Fawzi ............... A61F 2/013 606/200 |
| 2006/0293706 | A1 | 12/2006 | Shimon |
| 2007/0027534 | A1 | 2/2007 | Bergheim et al. |
| 2007/0060944 | A1 | 3/2007 | Boldenow et al. |
| 2007/0073246 | A1 | 3/2007 | Simon |
| 2008/0027481 | A1 | 1/2008 | Gilson et al. |
| 2009/0149881 | A1 | 6/2009 | Vale et al. |
| 2010/0274277 | A1 | 10/2010 | Eaton |
| 2010/0312268 | A1* | 12/2010 | Belson ............... A61F 2/01 606/200 |
| 2012/0016408 | A1 | 1/2012 | Barbut et al. |
| 2012/0109182 | A1 | 5/2012 | Belson |
| 2013/0035716 | A1 | 2/2013 | Belson |
| 2013/0035717 | A1 | 2/2013 | Belson |
| 2013/0096606 | A1 | 4/2013 | Bruchman et al. |
| 2013/0245669 | A1 | 9/2013 | Basu et al. |
| 2014/0058372 | A1 | 2/2014 | Belson |
| 2014/0155929 | A1 | 6/2014 | Belson |
| 2014/0249568 | A1 | 9/2014 | Adams et al. |
| 2015/0066075 | A1 | 3/2015 | Russell et al. |
| 2015/0320540 | A1 | 11/2015 | Belson |

FOREIGN PATENT DOCUMENTS

| | | |
|---|---|---|
| JP | 2007527264 A | 9/2007 |
| WO | WO-03094791 A2 | 11/2003 |
| WO | WO-2004019817 A1 | 3/2004 |
| WO | WO-2009038799 A1 | 3/2009 |

OTHER PUBLICATIONS

European search report and search opinion dated Apr. 17, 2015 for EP Application No. 13733627.7.
International search report and written opinion dated Apr. 9, 2008 for PCT/US2007/024558.
International search report and written opinion dated Apr. 22, 2013 for PCT Application No. US2013/20563.
"International search report and written opinion dated Dec. 14, 2015 for PCT/US2015/049908."
International search report dated Jan. 15, 2004 for PCT/US2003/026938.
Notice of allowance dated Feb. 26, 2013 for U.S. Appl. No. 13/648,986.
Notice of allowance dated Mar. 1, 2013 for U.S. Appl. No. 13/343,538.
Notice of allowance dated Apr. 15, 2015 for U.S. Appl. No. 12/532,630.
Notice of allowance dated Jul. 14, 2016 for U.S. Appl. No. 13/735,864.
Notice of allowance dated Aug. 10, 2012 for U.S. Appl. No. 13/347,046.
Notice of Allowance dated Nov. 1, 2013 for U.S. Appl. No. 13/648,992.
Notice of Allowance dated Nov. 18, 2013 for U.S. Appl. No. 13/866,887.
Notice of Allowance dated Nov. 23, 2011 for U.S. Appl. No. 10/493,854.
Office action dated Jan. 17, 2012 for U.S. Appl. No. 12/532,630.
Office action dated Jan. 17, 2013 for U.S. Appl. No. 13/648,992.
Office action dated Jan. 24, 2014 for U.S. Appl. No. 13/735,864.
Office action dated Feb. 11, 2009 for U.S. Appl. No. 10/493,854.
Office action dated Feb. 26, 2008 for U.S. Appl. No. 10/493,854.
Office action dated Feb. 26, 2014 for U.S. Appl. No. 12/532,630.
Office action dated Mar. 13, 2013 for U.S. Appl. No. 12/532,630.
Office action dated Apr. 10, 2012 for U.S. Appl. No. 13/343,538.
Office action dated Apr. 10, 2013 for U.S. Appl. No. 12/532,630.
Office action dated Jun. 10, 2013 for U.S. Appl. No. 12/532,630.
Office action dated Jul. 12, 2011 for U.S. Appl. No. 10/493,854.
Office action dated Jul. 17, 2013 for U.S. Appl. No. 13/735,864.
Office action dated Jul. 23, 2013 for U.S. Appl. No. 13/648,992.
Office action dated Jul. 23, 2013 for U.S. Appl. No. 13/866,887.
Office action dated Aug. 20, 2010 for U.S. Appl. No. 10/493,854.
Office action dated Aug. 25, 2015 for U.S. Appl. No. 14/175,042.
Office action dated Sep. 14, 2011 for U.S. Appl. No. 10/493,854.
Office action dated Nov. 6, 2012 for U.S. Appl. No. 12/532,630.
Office action dated Nov. 6, 2015 for U.S. Appl. No. 14/801,850.
Office action dated Nov. 19, 2013 for U.S. Appl. No. 12/532,630.
Office action dated Dec. 11, 2012 for U.S. Appl. No. 13/343,538.
U.S. Appl. No. 13/866,887, filed Apr. 19, 2013.
U.S. Appl. No. 14/537,814, filed Nov. 10, 2014.

* cited by examiner

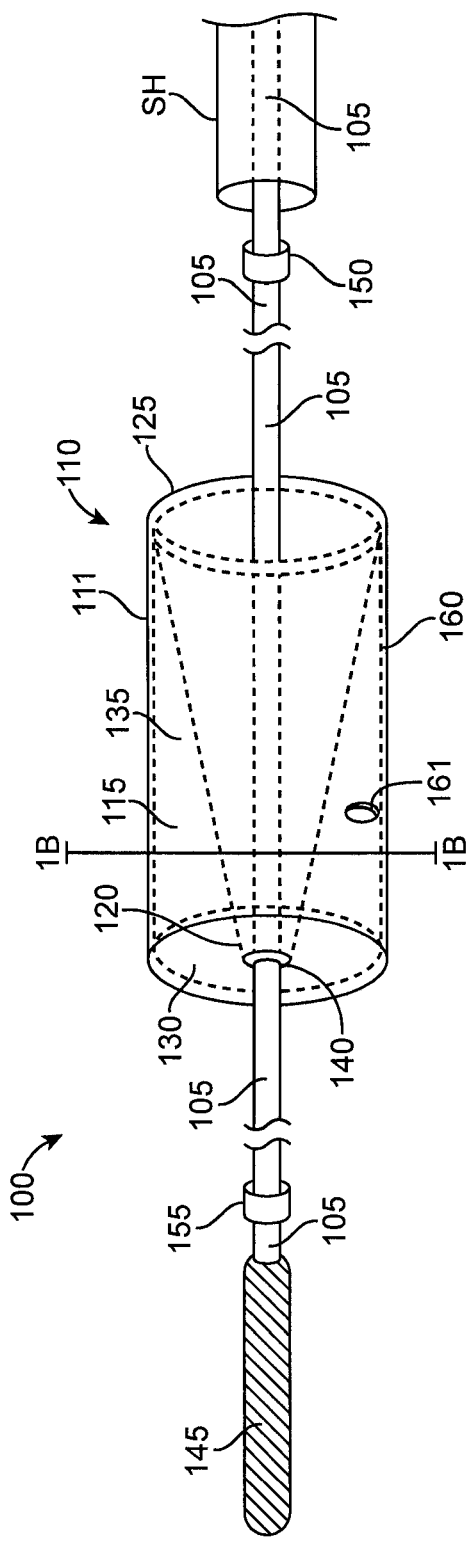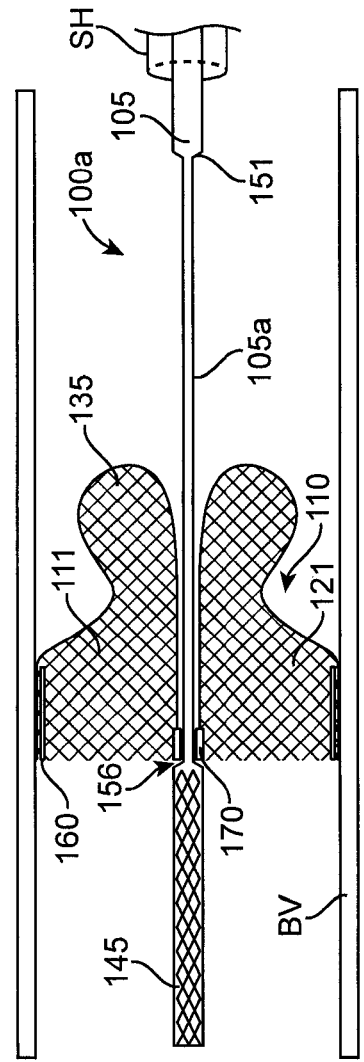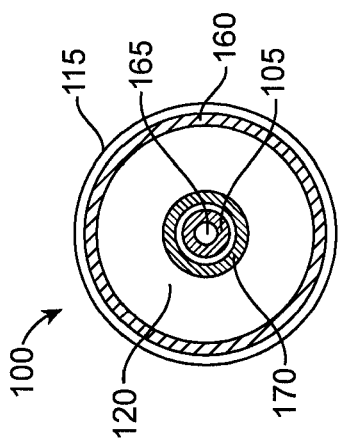

INTEGRATED EMBOLIC PROTECTION DEVICES

CROSS-REFERENCE TO RELATED APPLICATIONS

This application is a continuation of U.S. patent application Ser. No. 13/735,864, filed Jan. 7, 2013, now U.S. Pat. No. 9,492,265, which claims the benefit of U.S. Provisional Application No. 61/584,094, filed Jan. 6, 2012, and U.S. Provisional Application No. 61/738,852, filed Dec. 18, 2012, which applications are incorporated herein by reference.

BACKGROUND OF THE INVENTION

1. Field of the Invention

The present disclosure relates to medical devices, systems, and methods. In particular, the present disclosure relates to apparatus, systems, and methods for providing embolic protection in a patient's vascular system. More specifically, the present disclosure relates to embolic protection devices that can be deployed in a blood vessel to protect branch vessels and downstream organs from potential emboli during a catheter-based interventional procedure.

2. Background of the Invention

Cerebral embolism is a known complication of cardiac surgery, cardiopulmonary bypass, catheter-based interventional cardiology and electrophysiology procedures, and many other surgical procedures. Embolic particles, which may include thrombus, atheroma, and lipids, may become dislodged by surgical or catheter manipulations and enter the bloodstream, embolizing in the brain or other vital organs downstream. Cerebral embolism can lead to neuropsychological deficits, stroke, and even death. Other organs downstream can also be damaged by embolism, resulting in diminished function or organ failure.

Prevention of embolism would benefit patients and improve the outcome of many surgical procedures. Many current devices for preventing cerebral embolism may be less than ideal in various respects. For example, such current devices may involve multiple components and multiple steps, making the use of such devices cumbersome and even injury-prone for the patient. Also, when used with other catheter-based interventional tools, the patient's vasculature may need to be accessed at multiple points and through multiple paths. For example, a current embolic protection device may be advanced into the aortic arch through the descending aorta while other catheter-based interventional tools may then need to be advanced into or into proximity with the heart through other blood vessels including the vena cava, the right common carotid artery, and the left common carotid artery. Therefore, improved devices, systems, and methods for prevention or embolism that overcome at least some of the aforementioned short-comings are desired.

Previous devices for preventing cerebral embolism are described in the following patent application and patent publications: U.S. Pub. No. 2010/0312268 to Belson, entitled "Embolic Protection Device"; U.S. Pub. No. 2004/0215167 to Belson, entitled "Embolic Protection Device"; U.S. Pub. No. 2003/0100940 to Yodfat, entitled "Implantable Intraluminal Protector Device and Method of Using Same for Stabilizing Atheromoas"; PCT Pub. No. WO/2004/019817 to Belson, entitled "Embolic Protection Device"; U.S. Pat. No. 6,537,297 to Tsugita et al., entitled "Methods of Protecting a Patient from Embolization During Surgery"; U.S. Pat. No. 6,499,487 to McKenzie et al., entitled "Implantable Cerebral Protection Device and Method of Use"; U.S. Pat. No. 6,371,935 to Macoviak et al., entitled "Aortic Catheter with Flow Divider and Methods for Preventing Cerebral Embolization"; U.S. Pat. No. 6,361,545 to Macoviak et al., entitled "Perfusion Filter Catheter"; U.S. Pat. No. 6,254,563 to Macoviak et al., entitled "Perfusion Shunt Apparatus and Method"; U.S. Pat. No. 6,139,517 to Macoviak et al., entitled "Perfusion Shunt Apparatus and Method"; and U.S. Pat. No. 5,769,819 to Barbut et al., entitled "Cannula with Associated Filter."

SUMMARY OF THE INVENTION

The present disclosure provides devices, systems, and methods that overcome at least some of the short-comings of many current embolic protection devices discussed above. Prevention of embolism would benefit patients and improve the outcomes of many catheter-based interventional procedures. Given that potential emboli are often dislodged during catheter-based procedures, it would be advantageous to deploy an embolic protection system as part of a catheter-based vascular procedure or along with the sheath that is to be used during the procedure. The embolic protection system can be integrated on the catheter that is being used to perform the procedure, such as a transcatheter valve delivery system or an electrophysiology catheter, or be integrated on the sheath that is being used to perform the procedure, such as is used with a transcatheter valve delivery system or an electrophysiology catheter. Other embolic protection systems require separate procedural steps for installing the protector prior to the interventional or diagnostic procedure and removing the protector after the procedure. In many cases, a different access site is required as well. By having an embolic protection device integrated with the catheter or access sheath, extra procedural steps and the need for an extra access site can both be minimized. Where the embolic protection device is integrated with an access sheath, a conventional sheath can simply be replaced with one with an integrated embolic protection device, minimizing the need for extra devices. Where the embolic protection device is integrated with a catheter, such integration may in many cases not increase the overall diameter of the catheter. Also, the integrated embolic protection device may be mounted on the catheter with a slidable connection so that the catheter can freely slide through the embolic protection device after it has been deployed in a blood vessel.

An aspect of the present disclosure provides a catheter with an integrated embolic protection device or element. The catheter comprises a shaft, an embolic filter, and at least one of a proximal or distal stop. The catheter shaft has a lumen and a distal portion. The embolic filter is slidably mounted over the distal portion of the shaft. The filter comprises a port for the passage of the shaft therethrough and a porous mesh material. The porous mesh material defines a collection chamber for captured emboli. The filter has a collapsed configuration and a deployed configuration. In the deployed configuration, an outer periphery of the filter contacts a blood vessel wall to direct blood flow and potential emboli into the collection chamber. The proximal stop limits the proximal movement of the embolic filter on the distal portion of the shaft while the distal stop limits the distal movement of the embolic filter. A resilient seal may be positioned within the catheter port for forming a seal around the shaft passing through the filter port.

Typically, the porous mesh material will comprise a cylindrical outer portion and a conical inner portion. The conical inner portion is positioned inside the cylindrical outer portion and has a wider proximal end joined to the cylindrical outer portion and a narrow distal end coupled to the shaft passage port. The distal end of the embolic filter is open for blood to flow between the conical inner portion and the cylindrical outer portion. The space between the conical inner portion and the cylindrical outer portion defines the collection chamber for captured emboli.

Typically, a stent-like support scaffold will be coupled to the cylindrical outer portion of the porous mesh material for supporting the cylindrical outer portion. The stent-like support scaffold can have a collapsed configuration and an expanded configuration. The stent-like support scaffold self-expands into the expanded configuration when the filter is in the deployed condition. The stent-like support scaffold may be made of a resilient metal, polymer material, a malleable material, a plastically deformable material, a shape-memory material, or combinations thereof.

The catheter may further comprise structures to facilitate the collapse of the embolic filter back into the collapsed configuration after deployment. The catheter may comprise a pull loop or other graspable structure coupled to the distal end of the cylindrical outer portion for closing the collection chamber. At least one retraction member may be coupled to the cylindrical outer portion for facilitating the retraction of the embolic filter into the undeployed configuration.

In some cases, the cylindrical outer portion comprises at least one closeable side port for the introduction of a second catheter, guide-wire, delivery sheath, or other surgical tool therethrough. This side port can be useful for operations where the use of multiple catheters or interventional tools is required and embolic protection is still desired.

The porous mesh material of the embolic filter can have many properties. It may have a collapsed configuration and an expanded configuration. It may self-expand into the expanded configuration when it is in the deployed configuration. It may comprise a fabric of knitted, woven, or nonwoven fibers, filaments, or wires having a pore size chosen to prevent emboli over a predetermined size from passing through. It may be made of a resilient metal, polymer material, or combinations thereof, a malleable or plastically deformable material, or a shape-memory material. It may have an antithrombogenic coating on its surface. It may have a pore size in the range of about 1 mm to about 0.1 mm to prevent emboli above a certain size from passing through while allowing the passage of blood.

The shaft passage port of the embolic filter may be configured to form a seal to prevent passage of emboli over a predetermined size therethrough.

The embolic filter may be slidably mounted on the distal portion of the shaft in many ways. The distal portion of the shaft may comprise a low-profile portion over which the embolic filter is slidably mounted. In this case, the proximal stop may comprise a proximal end of the low-profile portion and the distal stop may comprise a distal end of the low-profile portion. Alternatively or in combination, the proximal stop may comprise a proximal stop member and the distal stop may comprise a distal stop member, with both stop members being attached or otherwise coupled to the distal portion of the shaft. In some cases, these proximal and distal stops may be integral with the catheter shaft.

At least one of the shaft, embolic filter, proximal stop, or distal stop may be radiopaque or comprise a radiopaque marker to facilitate the viewing of the catheter and its parts during a surgical procedure.

The catheter can be inserted through a tubular outer delivery sheath. The tubular outer delivery sheath maintains the embolic filter in the undeployed retracted condition when the embolic filter is therewithin. The embolic filter will be free to deploy into the deployed expanded configuration when the embolic filter is advanced out of the tubular outer delivery sheath.

The distal end of the shaft may be coupled to a valve replacement delivery element, an expandable structure for balloon valvuloplasty, an energy delivery element for ablation, or other transcatheter surgical element.

Another aspect of the present disclosure provides a system for catheter-based interventional procedures. The system comprises the catheter described above and a tubular outer delivery sheath through which the catheter is advanced.

Yet another aspect of the present disclosure provides an introducer sheath with an integrated embolic protection device or element. This introducer sheath can be used for the delivery of surgical instruments and comprises a tubular member and an embolic filter. The tubular member has a central lumen and a distal portion. The embolic filter is coupled to the distal portion of the shaft. The filter comprises a porous mesh material defining a collection chamber for captured emboli. The filter has a collapsed configuration and a deployed configuration. In the deployed configuration, an outer periphery of the filter contacts a blood vessel wall to direct blood flow and potential emboli into the collection chamber.

The embolic filter can be collapsed or constrained in many ways. In one example, the embolic filter is coupled to an exterior of the distal portion of the tubular member and is collapsed into the collapsed configuration by an exterior constraining member. The exterior constraining member may be a tube slidable over the tubular member. In another example, the embolic filter is collapsed by retraction of the filter into the central lumen of the tubular member. Here, the embolic filter is coupled to an internal tube or wire structure disposed in the central lumen of the tubular member for retraction of the embolic filter into the central lumen.

Typically, the porous mesh material comprises a cylindrical outer portion and a conical inner portion. When the embolic filter is in the deployed configuration, the conical inner portion is positioned inside the cylindrical outer portion. The conical inner portion has a wider proximal end joined to the cylindrical outer portion and a narrow distal end coupled to the distal portion of the tubular member. The distal end of the embolic filter is open for blood to flow between the conical inner portion and the cylindrical outer portion. The space between the conical inner portion and the cylindrical portion defines the collection chamber for captured emboli.

The sheath may further comprise a stent-like scaffold coupled to the cylindrical outer portion of the porous mesh material for supporting the cylindrical outer portion. It may have a collapsed configuration and an expanded configuration, and may self-expand into the expanded configuration when the filter is in the deployed condition. It may be made of a resilient metal, polymer material, a malleable material, a plastically deformable material, a shape-memory material, or combinations thereof.

The introducer sheath may include further structures to facilitate the collapse of the embolic protection element. The sheath may further comprise a pull loop or other graspable structure coupled to the distal end of the cylindrical outer portion for closing the collection chamber. The sheath may further comprise at least one retraction member coupled to the cylindrical outer portion for facilitating the retraction of the embolic filter into the undeployed configuration.

In some cases, the cylindrical outer portion may comprise at least one closeable side port for the introduction of a second catheter, guide-wire, delivery sheath, or other surgical tool therethrough.

The porous mesh material of the embolic filter can have many properties. It may be made of a resilient metal, polymer material, a malleable material, a plastically deformable material, a shape-memory material, or combinations thereof. It may have an antithrombogenic coating on its surface. It may have a pore size in the range of about 1 mm to about 0.1 mm.

At least one of the tubular member or embolic filter may be radiopaque or comprise a radiopaque marker.

Yet another aspect of the present disclosure provides a system for catheter-based interventional procedures. The system comprises the above described introducer sheath and a catheter deliverable through the central lumen of the introducer sheath. The catheter can be coupled to a valve replacement delivery element, an expandable structure for balloon valvuloplasty, an energy delivery element for ablation, or other transcatheter surgical element.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A is a side view of a catheter with an integrated embolic protection device according to an embodiment of the invention;

FIG. 1B is a cross-sectional view of the catheter of FIG. 1A;

FIG. 1C is a side cross-sectional view of a catheter with an integrated embolic protection device according to another embodiment of the invention;

DETAILED DESCRIPTION OF THE INVENTION

Figure 1D:
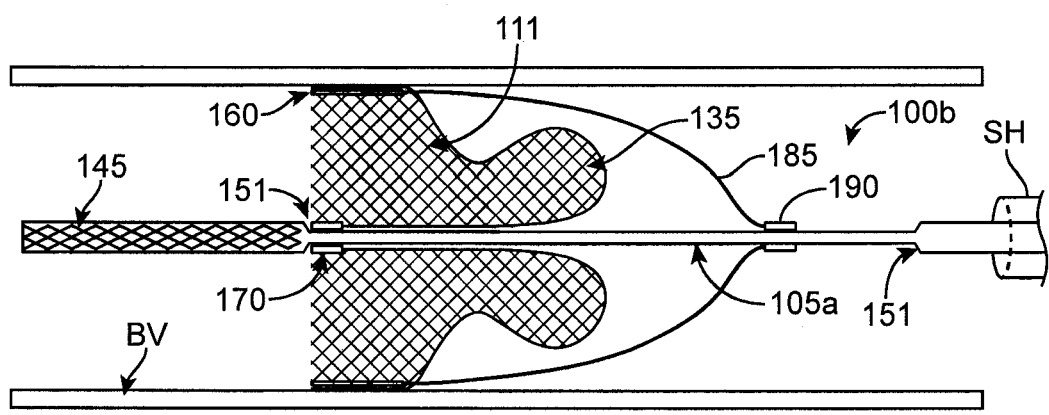
FIG. 1D is a side cross-sectional view of a catheter with an integrated embolic protection device according to yet another embodiment of the invention.

Aspects of the disclosure provide improved devices, systems, and methods for the prevention of embolisms in a catheter-based interventional procedure. In particular, catheters and sheaths with integrated embolic protection devices or elements are provided. Various aspects of the disclosure described herein may be applied to any of the particular applications set forth below or for any other types of catheter or access sheath for catheters. It shall be understood that different aspects of the disclosure can be appreciated individually, collectively, or in combination with each other.

1. Catheter with Integrated Embolic Protection Device

According to an aspect of the present disclosure, a catheter for a catheter-based interventional procedure can itself be provided with an integrated embolic protection device or element. FIG. 1A is a side view of a catheter 100 with an integrated embolic protection device or element 110. The integrated embolic protection device or element 110 is shown in its deployed configuration in FIG. 1A. The catheter 100 may be advanced into a surgical site through delivery sheath SH. The integrated embolic protection element 110 has a collapsed configuration when it is constrained by delivery sheath SH. The embolic protection element 110 is allowed to expand into the deployed configuration when it is advanced out of the distal end of the delivery sheath SH. For example, at least a portion of the integrated embolic protection element 110 may be self-expanding and self-supporting.

The catheter 100 may optionally include a shoulder positioned proximal to the embolic protection element 110 to maintain the position of the embolic protection element 110 on the catheter 100 as the delivery sheath SH is withdrawn during deployment. Alternatively, a pusher catheter that fits in-between the catheter 100 and the delivery sheath SH may be used to facilitate deployment.

The catheter 100 comprises a catheter shaft 105 that the integrated embolic protection element 110 is mounted over. The integrated embolic protection element 110 comprises a porous mesh material 111, which acts as a filter. The porous mesh material 111 comprises two main sections, a cylindrical outer structure 115 and a conical inner structure 120. The cylindrical outer structure 115 is deployed adjacent to the blood vessel wall to protect branch vessels. The central conical inner structure 120 is deployed within the center of the vessel lumen to provide protection to downstream circulation. An upstream or distal end 130 of the embolic protection element 110 opens into a space between the cylindrical outer structure 115 and the conical inner structure 120. This space defines an embolic collection chamber 135 for capturing emboli.

The catheter 100 may be configured as a diagnostic catheter, a guiding catheter, or a therapeutic catheter. As shown in FIG. 1A, the distal end of the catheter shaft 105 will typically be coupled with an interventional element 145. The interventional element 145 may comprise a cardiac valve replacement implant delivery device, an expandable structure for balloon valvuloplasty, an energy delivery element for ablation, or any number of other structures for catheter-based surgery, implantation, electrophysiological procedures, or other procedures.

The integrated embolic protection element 110 comprises a port 140, which is coupled to the distal portion of the shaft 105. As shown in FIG. 1A, the port 140 is coupled to a distal or upstream end of the conical inner structure 120. The port 140 is sealed tight enough against the shaft 105 so that no emboli may pass through the space between the port 140 and the shaft 105. In some embodiments, the integrated embolic protection element 110 will be fixedly mounted on the distal portion of the catheter shaft 105. Typically, the integrated embolic protection element 110 will be slidably mounted over the distal portion of the catheter shaft 105. The shaft

105 may further comprise a downstream or proximal stop 150 which limits proximal movement of the embolic protection element 110 on the shaft 105 and an upstream or distal stop 155 which limits distal movement of the embolic protection element 110 on the shaft 105.

The porous mesh material 111 may be made of knitted, woven, or non-woven fibers, filaments or wires and will have a pore size (e.g., from about 1 mm to about 0.1 mm) chosen to allow blood to pass through but prevent emboli above a certain size from passing through. The porous mesh material may be made of a metal, a polymer, or a combination thereof and may optionally have an antithrombogenic coating on its surface (e.g., the porous mesh material 111 may be heparinized).

The embolic protection element 110 will preferably be self-supporting in the deployed configuration. In some embodiments, the porous mesh material 110 may be made of a shape-memory material so that it may self-expand when no longer constrained by sheath SH and collapse into a low-profile configuration when constrained by sheath SH. The embolic protection element 110 will also preferably maintain sufficient contact with the target vessel wall to form an adequate seal to prevent emboli above a certain size from passing around the outside of the embolic protection element 110.

Typically, the cylindrical outer structure 115 will be supported by a stent-like support structure 160. The stent-like support structure 160 provides support to the porous mesh material 110 and maintains an adequate seal against the vessel wall. The stent-like support structure 160 may comprise a framework that includes one or more longitudinal struts and hoops that form the support structure 160. The hoops and struts may be made of a shape memory material so that it may self-expand when no longer constrained by sheath SH and collapse into a low-profile configuration when constrained by sheath SH. Alternatively, the hoops and struts may be made of a resilient metal and/or polymer material to make a self-expanding framework or a malleable or plastically deformable material to make a framework that can be expanded with an inflatable balloon or other expansion mechanism. The porous mesh material 110 supported on the framework can be resilient, flaccid, or plastically deformable. Hybrid constructions that combine features of the self-supporting structure and the frame-supported structure may also be used. Hybrid deployment methods, such as balloon-assisted self-expansion can also be utilized.

In some embodiments, the stent-like support structure 160 may comprise a side port 161 through which a second catheter or other interventional device may be passed through to access a surgical site. The side port 161 may be collapsible and closeable so that no emboli passed through the side port 161 when it is not being used. Alternatively, the porous mesh material 110 and the stent-like support structure 160 may be resilient enough so that a second catheter or other interventional device may be passed through its pores to access a surgical site without permanently affecting the pore sizes of the aforementioned structures.

FIG. 1B is a cross-sectional view of the catheter 100 taken along line 1B in FIG. 1A. As shown in FIG. 1B, the support structure 165 is coupled to the cylindrical outer structure 115. The catheter shaft 105 comprises a central lumen 165, and the port 140 comprises a sliding mechanism 170. The catheter 100 may be delivered with the embolic protection element 110 in the undeployed or collapsed configuration over a guide-wire disposed within the central lumen 165.

In many embodiments, the sliding mechanism 170 need not make a perfect hemostatic seal. Preferably, the sliding mechanism 170 should exclude the passage of emboli above a certain size therethrough. The sliding mechanism 170 can comprise one or more rings, roller bearings, or other structures that allow the embolic protection element 110 to slide freely on the catheter shaft 105. The sliding mechanism 170 will preferably have a low coefficient of friction and/or a lubricious coating so that movement of a catheter shaft 105 through the sliding mechanism 170 will not jostle or dislodge the embolic protection element 110. In alternative embodiments, the sliding mechanism 170 can contain an additional sealing element, such as resilient flaps, an iris structure, an expandable sealing material, or the like.

FIG. 1C is a side cross-sectional view of a catheter 100*a* that is generally similar to the catheter 100 described above. In catheter 100*a*, the integrated embolic protection device 110 is mounted over a low-profile section 105*a* of catheter shaft 105 to minimize the overall diameter or "profile" of the collapsed embolic protection device 110 and catheter shaft 105. The catheter shaft 105 can comprise a downstream or proximal transition point 151 where the shaft 105 transitions from having a low-profile to having a normal profile. This transition point 151 can act as a downstream or proximal stop 151 to limit the proximal movement of the integrated embolic protection device 110. Likewise, the catheter shaft 105 can further comprise an upstream or proximal transition point 156 which can act as an upstream or distal stop 156 to limit the distal movement of the integrated embolic protection device 110.

As shown in FIG. 1C, the sliding mechanism 170 may be attached to the reduced diameter section 105*a* of the catheter shaft 105. Preferably, the diameter of the undeployed embolic protection element 110 when retracted onto the reduced diameter section 105*a* will be no larger than the largest section of the catheter 100, which will typically be the region of the interventional element 145 at the distal end of the catheter shaft 105. Downstream or proximal of the interventional element 145, the catheter shaft 105 can be reduced in size to allow integration of the embolic protection element 110 without changing the overall tracking profile of the catheter 100. In some embodiments, the overall tracking profile of the catheter 100 may be as small as 8 to 9 French or even smaller.

As shown in FIG. 1A, the wider end of the conical inner structure 120 is on the proximal or upstream side. Alternatively, the wider end of the conical inner structure 120 may be on the distal or upstream side as shown in FIGS. 1C to 1E.

The embolic protection element 110 can be retracted and withdrawn with the catheter shaft 105 after the desired diagnostic or interventional procedures has been completed. In many embodiments, the catheter 100 includes features to assist in retracting the device for retrieval from a target site such as the patient's aorta. Examples of such features are shown in FIGS. 1D and 1E.

FIG. 1D is a side cross-sectional view of a catheter 100*b* that is generally similar to catheter 100*a* described above. The catheter 100*b* further comprises a conical guiding structure 185, which is slidably coupled to the catheter shaft downstream of or proximal to the embolic protection element 110 with a sliding mechanism 190. The conical guiding structure 185 may comprise one or more curved arms coupling the outer cylindrical structure 115 and/or the stent-like support structure 160 with the catheter shaft 105. In some embodiments, the conical guiding structure 185 may be integral with the stent-like support structure 160, i.e., the stent-like support structure 160 may comprise a cylindrical upstream or distal portion and a conical downstream or proximal portion that acts as a conical guiding structure. The conical guiding structure 185 assists the embolic protection element 110 in collapsing when the sheath SH is advanced along the conical guiding structure 185. In some embodiments, the upstream or distal end of the conical guiding structure 185 may be coupled to the outer cylindrical structure 115 and/or the stent-like support structure 160, and gradual distal advancement of the sheath SH will cause the conical guiding structure 185 to gradually collapse the embolic protection element 110.

Figure 1E:
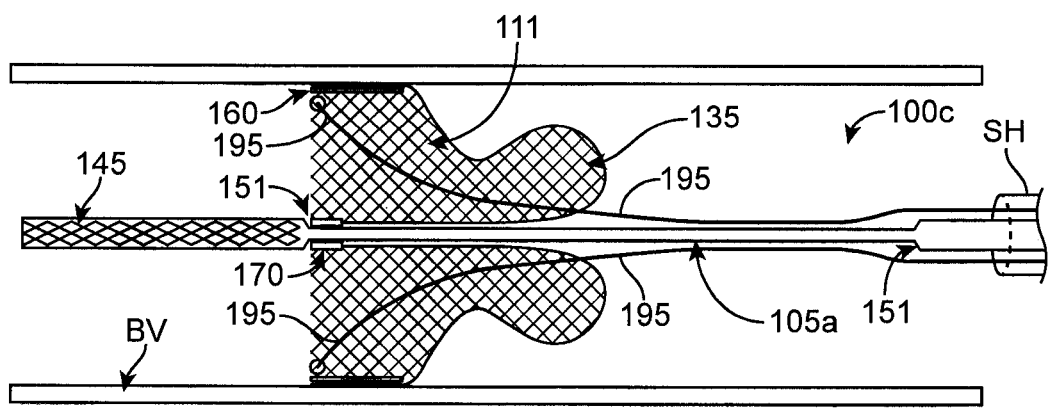
FIG. 1E is a side cross-sectional view of a catheter with an integrated embolic protection device according to yet another embodiment of the invention.

FIG. 1E is a side cross-sectional view of a catheter 100b that is generally similar to catheter 100a described above. The catheter 100b further comprises tethers 195. The tethers 195 may be made of suture, wire, plastic filament, or a combination thereof. The tethers 195 are disposed within a circumferential loop of the porous mesh material at the upstream or distal end of the outer cylindrical structure 115. The tethers 195 lead back into the sheath SH where they can be pulled back by a user at the user end of the sheath SH. The tethers 195 can act as drawstrings to close the upstream or distal end of the outer cylindrical structure 115, thereby closing off the emboli collection chamber 135. It may be desirable to first close off the emboli collection chamber 135 to seal any emboli and potential emboli inside before the embolic protection element 110 is retracted into the sheath SH. This initial sealing can assure that any captured emboli do not migrate out of the embolic protection element 110.

Further tethers or retraction members may be provided to similarly close off one or more other sections of the embolic protection element 110. The tethers or retraction members may also serve as retraction members to facilitate the retraction and collapsing of the embolic protection element 110 into the sheath SH. For example, the downstream or proximal end of the cylindrical outer structure 115 may be coupled to one or more tethers or retraction members that can be retracted to reduce the circumference of the cylindrical outer structure 115. In some embodiments, a pool loop or other graspable structure near the downstream or proximal end of the embolic protection element 110 is connected to the tethers or retraction members by one or more connecting members.

For catheters 100, 100a, 100b, and 100c shown in FIGS. 1A to 1E, the embolic protection element 110 may be constructed with the porous mesh material 111 and the stent-like support structure 160 having approximately the relative longitudinal dimensions shown in the drawings. The porous mesh material 111 and the stent-like support structure 160, however, can each be made longer or shorter without adversely affecting the performance of the embolic protection element 110.

The entire catheter 100 or portions of it may be coated with an anti-thrombogenic coating, for example, a bonded heparin coating, to reduce the formation of clots that could become potential emboli. Alternatively or in addition, the entire catheter 100 or portions of it may have a drug-eluting coating containing an anti-inflammatory or antistenosis agent. The catheter 100 with an integrated embolic protection element 110 is described herein for protecting against cerebral embolisms but may be used for protecting against emboli in other organ systems. For example, the catheter 100 and embolic protection element 110 can be deployed in the patient's ascending aorta for preventing embolic particles in the aortic blood flow from entering the renal arteries and embolizing in the patient's kidneys. Alternatively or in addition, the entire catheter 100 or portions of it may be radiopaque to facilitate viewing of the catheter 100 as a procedure proceeds. Radiopaque markers may also be coupled to one or more portions of the catheter 100.

FIGS. 2A to 2D show a catheter-based interventional procedure using the catheter 100 with the integrated embolic protection element 110.

Figure 2A:
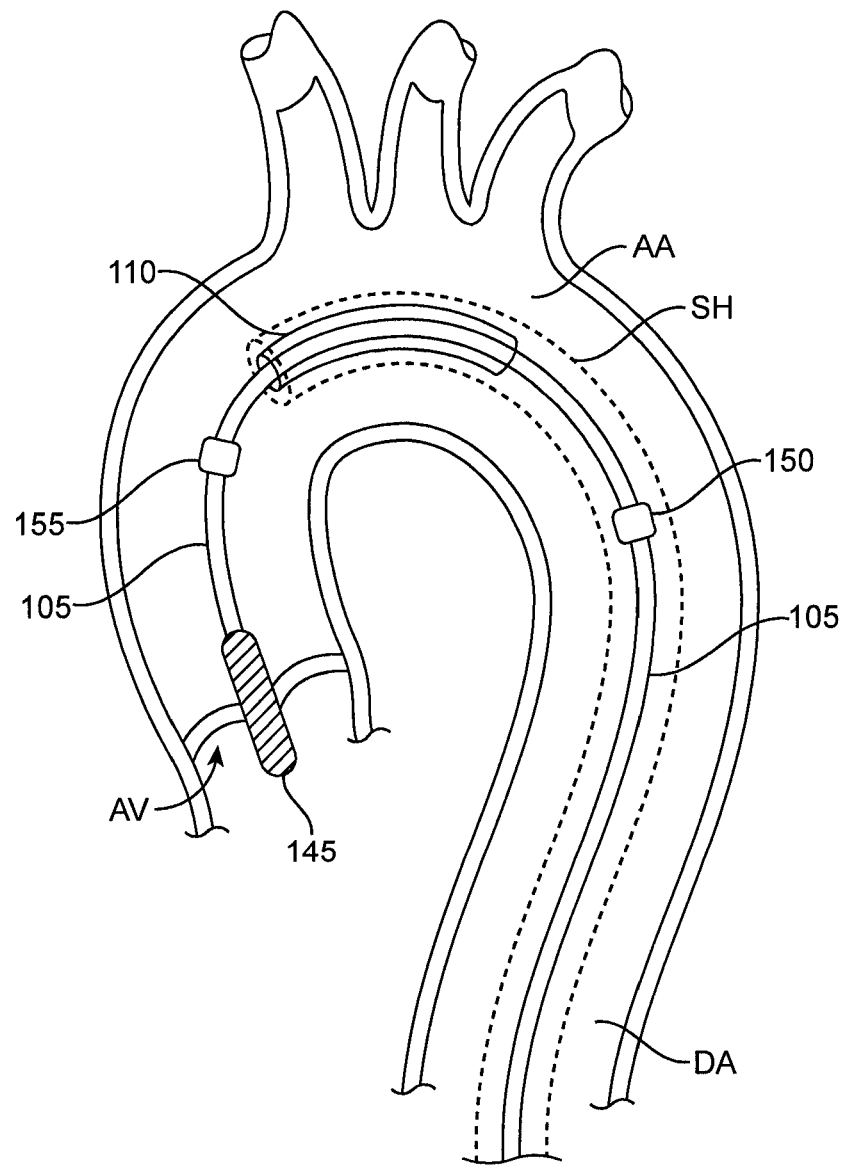
FIGS. 2A to 2D show a catheter-based interventional procedure using a catheter with an integrated embolic protection device according to embodiments of the invention.

FIG. 2A shows the catheter 100 with the integrated embolic protection element 110 held in the undeployed, collapsed configuration by the sheath SH. The catheter 100 has been inserted through the descending aorta DA so that the embolic protection element 110 within the aortic arch AA and the interventional element 145 advanced out through the sheath SH so that it is at the aortic valve AV. As shown in FIGS. 2A to 2D, the interventional element 145 is an aortic replacement valve delivery system. The catheter 100 and interventional element 145 may also be configured to deliver replacement valves for the mitral valve, the tricuspid valve, or the pulmonary valve. The catheter 100 and the interventional element 145 may also be used to other procedures such as any electrophysiological procedure, balloon valvuloplasty, and various ablative procedures, among others.

Figure 2B:
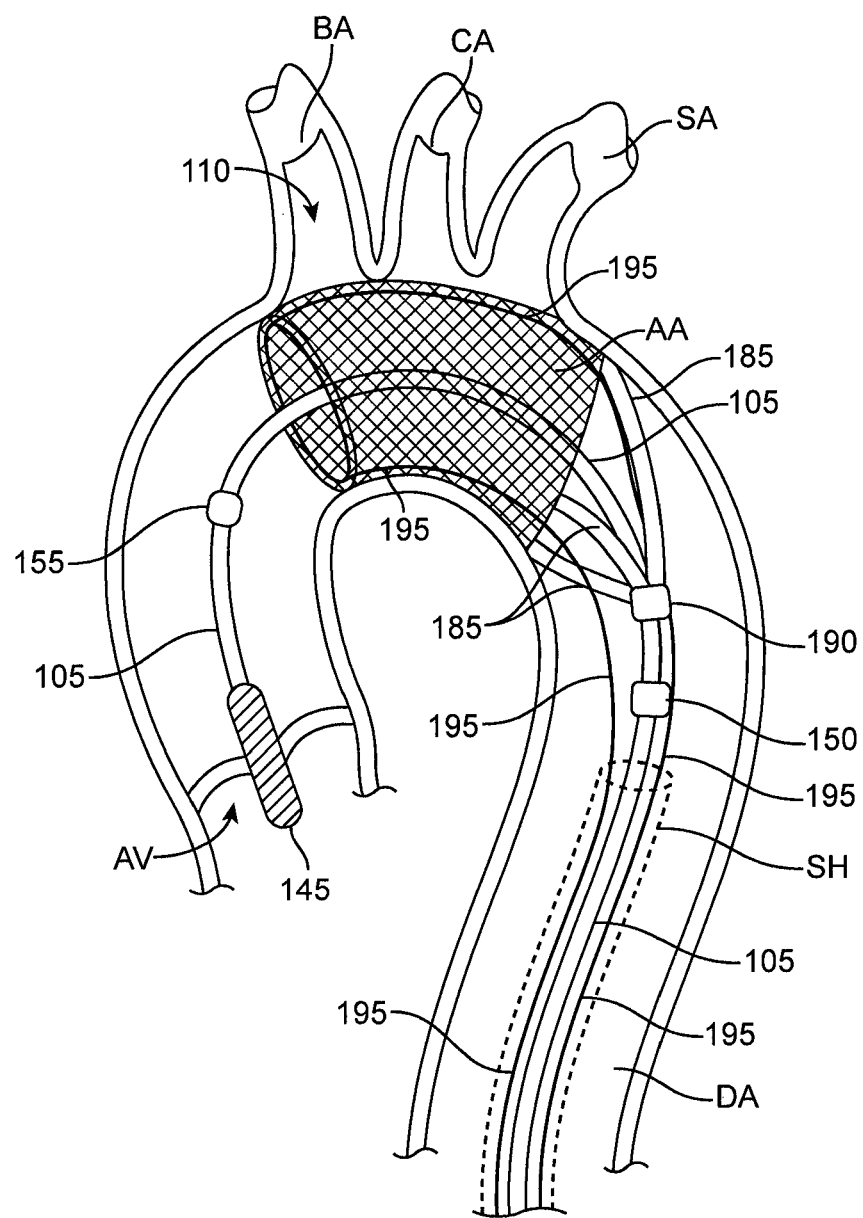

As shown in FIG. 2B, the sheath SH has been retracted to allow the embolic protection element 110 to expand to contact that vessel wall of the aortic arch AA. The embolic protection element 110 is positioned so as to prevent emboli above a certain size from entering the brachiocephalic artery BA, the left carotid artery CA, the left subclavian artery SA, and the descending aorta DA. As shown in FIG. 2B, the catheter 100 may comprise tethers 195 and the guiding structure 185, both described above, to facilitate retraction and collapsing of the embolic protection element 110. For ease of illustration, the tethers 195 and the guiding structure 185 are not shown in FIG. 2A.

Figure 2C:
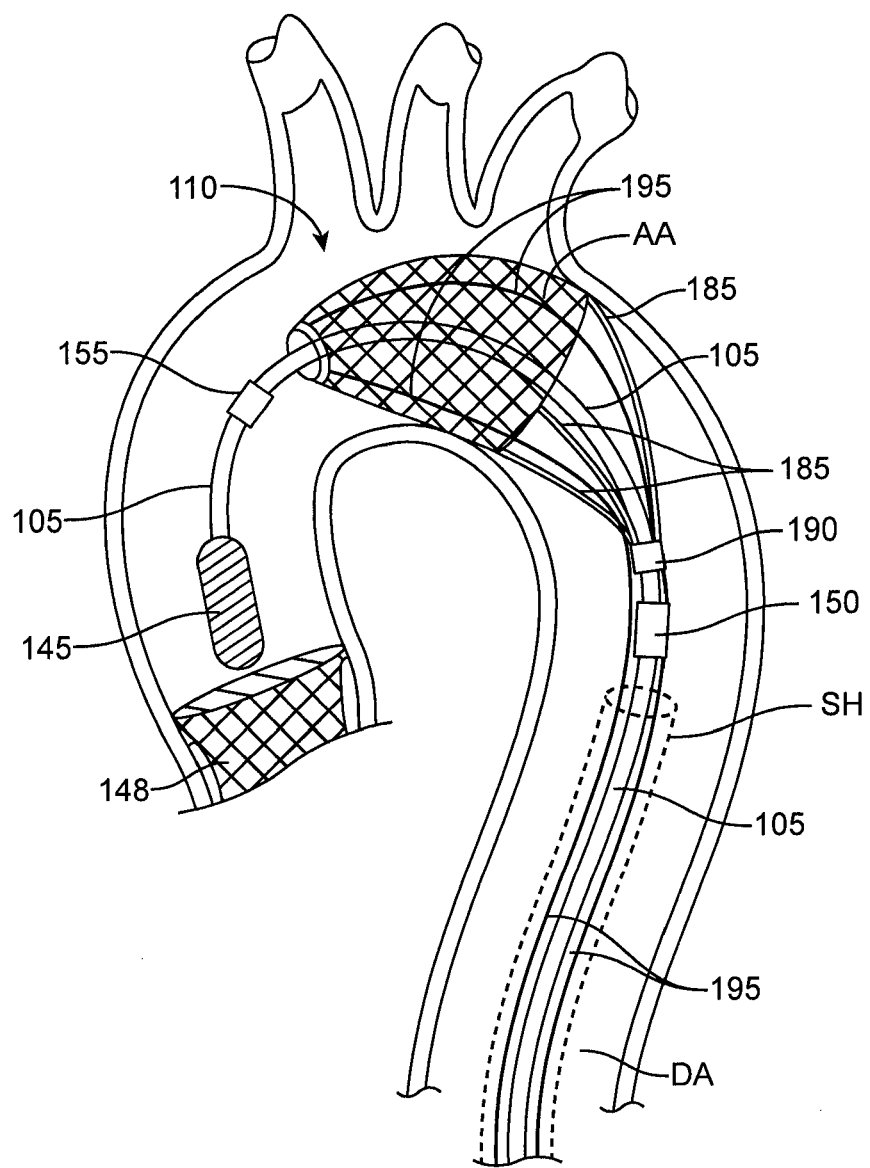

Once the desired interventional procedure has been performed, the embolic protection element 110 can be collapsed and the catheter 100 retracted. As shown in FIG. 2C, the interventional procedure performed is the delivery of an aortic valve replacement 148. As discussed above, other interventional procedures may instead be performed. As shown in FIG. 2C, the tethers 195 are retracted to close the upstream or distal end of the embolic protection element 110.

Figure 2D:
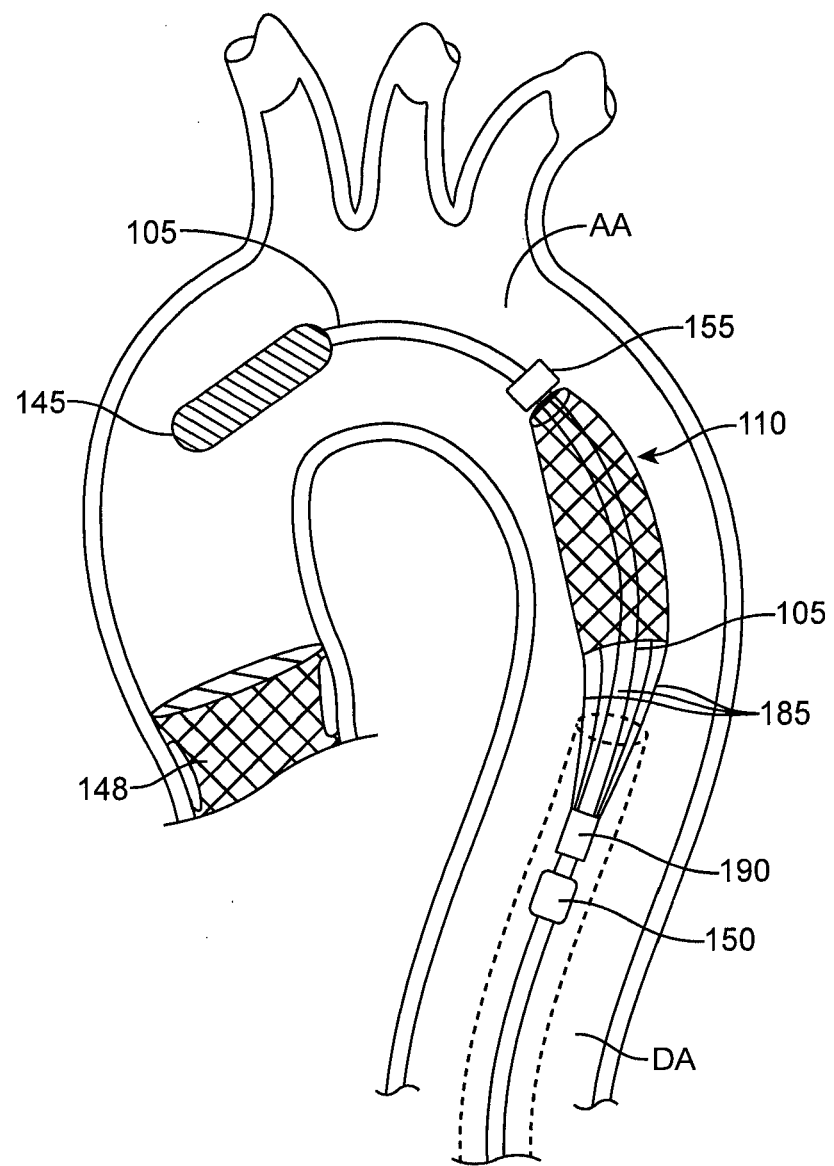

Once the upstream or distal end of the embolic protection element 110 is closed, the catheter shaft 105 can be retracted to begin to pull the embolic protection element 110 into the sheath SH. As shown in FIG. 2D, the conical guiding structure 185 facilitates the collapsing of the embolic protection element 110 as it is retracted. Once the catheter shaft 105, the interventional element 145, and the embolic protection element 110 are completely retracted into the access sheath, the catheter 100 and the sheath SH can be complete removed from the aortic arch AA, the descending aorta DA, and the patient's body. For ease of illustration, the tethers 195 are not shown in FIG. 2D.

2. Access Sheath with Integrated Embolic Protection Device

Figure 3A:
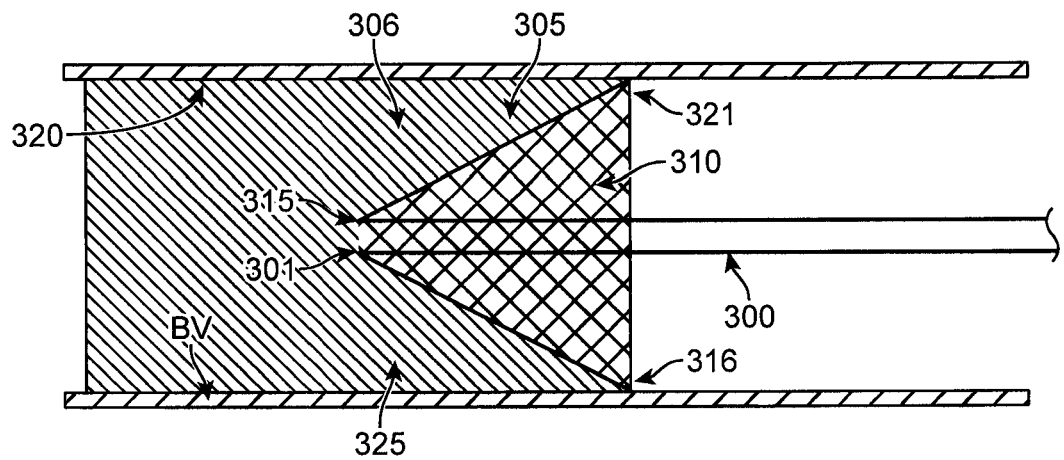
FIG. 3A is a side cross-sectional view of an access sheath with an integrated embolic protection device according to an embodiment of the invention.

According to another aspect of the present disclosure, a sheath used for a catheter-based interventional procedure can itself be provided with an integrated embolic protection device or element. FIG. 3A is a side cross-sectional view of an access sheath 300 with an integrated embolic protection element 305. For example, the access sheath 300 may be used in lieu of the sheath SH used in the procedure shown in FIGS. 2A to 2D or any other catheter-based interventional procedure. With the access sheath 300 having an integrated embolic element 305, any catheter, not just the catheter 100 with an integrated embolic element 110, can be used in a desired interventional procedure while enjoying the benefits of protection against emboli with minimum extra steps and parts as described in the present disclosure.

The integrated embolic protection element 305 may in many respects be similar to the integrated embolic protection element 105 described above. The integrated embolic protection element 305 is coupled to the distal end 301 of the access sheath 300 and comprises a porous mesh material 306. The porous mesh material 306 comprises a conical inner structure 310 coupled to a cylindrical outer structure 320. The upstream or distal end 315 of the conical inner structure 310 is coupled to the distal end 301 of the access sheath 300. The proximal or downstream end 316 of the conical inner structure 310 is coupled to the proximal or downstream end 321 of the cylindrical outer structure 320. The space between the conical inner structure 310 and the cylindrical outer structure 320 defines a collection chamber 325 for capturing emboli above a certain size.

The porous mesh material 306 may be made of a knitted, woven, or non-woven fibers, filaments, or wires and will have a pore size chosen to allow blood to pass through but prevent emboli above a certain size from passing through. The porous mesh material 306 may be made of a metal, a polymer, or a combination thereof and may optionally have an antithrombogenic coating on its surface.

The embolic protection element 305 will typically be in its undeployed configuration in or on the main tubular body of the sheath 300 as it is inserted into a blood vessel. The embolic protection element 305 will typically be deployed across especially critical branch vessels, such as across the aortic arch to cover the ostia of the cerebral arteries. The integrated embolic protection element 305 is shown in its expanded, deployed configuration in FIG. 3A, with the cylindrical outer structure 320 contacting the blood vessel wall By. When the sheath SH is positioned, advanced, or retracted within a patient's vasculature, however, the integrated embolic protection element 305 will typically need to be in its collapsed, undeployed configuration.

Figure 3B:
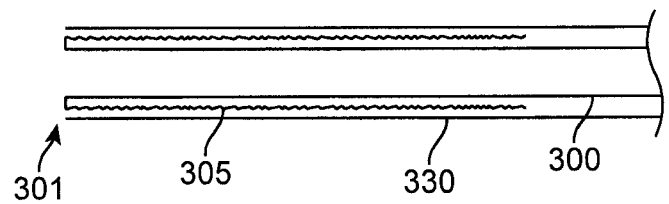
FIG. 3B is a side cross-sectional view of an access sheath with an integrated embolic protection device according to another embodiment of the invention.

The integrated embolic protection element 305 may be collapsed or constrained in many ways. For example, a larger diameter outer tube 330 may be provided as shown in FIG. 3B. The larger diameter outer tube 330 is disposed over the porous mesh material 306 to constrain it between the outer surface of the sheath 300 and the inner surface of the larger diameter outer tube 330. In such embodiments, the integrated embolic protection element 305 may be self-expanding such that it can assume the shape shown in FIG. 3A when the larger diameter outer tube 330 is retracted or when the sheath 300 is advanced out of the upstream or distal end of the larger diameter outer tube 330.

Figure 3C:
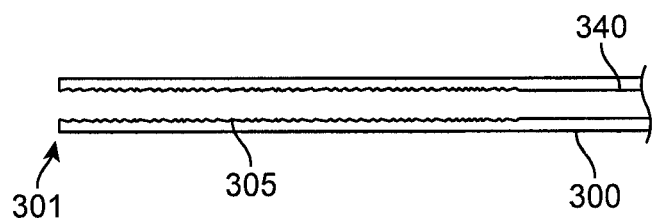
FIG. 3C is a side cross-sectional view of an access sheath with an integrated embolic protection device according to yet another embodiment of the invention.

In another example, the integrated embolic protection element 305 may be stored within the interior of the sheath 300 when the embolic protection element 305 is in its collapsed, undeployed configuration as shown in FIG. 3C. The sheath 300 may comprise retraction element 340 coupled to the embolic protection element 305. The retraction element 340 may be an inner tube or one or more inner arms that can be used to push the integrated embolic protection element 305 out of the tubular main body of the sheath 300 or to pull it back into the sheath 300. As the embolic protection element 305 is coupled to the distal end 301 of the sheath 300, the embolic protection element 305 everts out of the main body of the sheath 300 when it is advanced out.

The embolic protection element 305 will preferably be self-supporting in the deployed configuration. The embolic protection element 305 will also preferably maintain sufficient contact with the vessel wall to form an adequate seal to prevent emboli above a certain size from passing around the outside of the embolic protection element 305. For example, the porous mesh material 306 may be constructed with a resilient filter mesh material that can be compressed into the undeployed configuration and will self-expand into the deployed configuration.

Figure 3D:
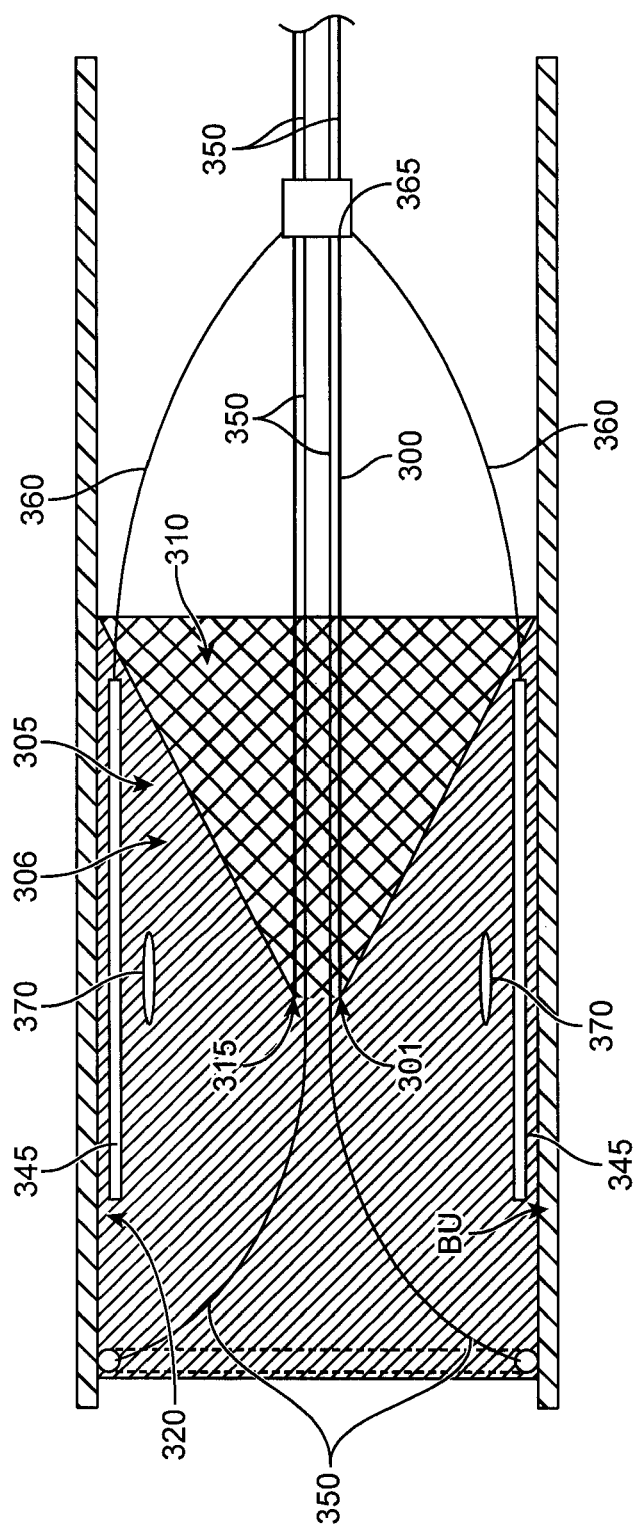
FIG. 3D is a side cross-sectional view of an access sheath with an integrated embolic protection device according to yet another embodiment of the invention.

As shown in FIG. 3D, the sheath 300 may comprise a stent-like support structure 345 similar to the stent-like support structure 160 described above for supporting the cylindrical outer structure 320. The stent-like support structure 345 may comprise a framework that includes one or more longitudinal struts or hoops that form a support structure and assist in the expansion and wall apposition of the embolic protection element 305. The hoops and struts may be made of a resilient metal and/or polymer material to make a self-expanding framework or malleable or plastically deformable material to make a framework that can be expanded with an inflatable balloon or other expansion mechanism. Alternatively, the framework can be made of a shape-memory material that can be used to deploy and/or retract the embolic protection element 305. The porous mesh material 306 supported on the framework 345 can be resilient, flaccid, or plastically deformable. Hybrid constructions that combine features of the self-supporting structure and the frame-supporting structure may also be used. Hybrid deployment methods, such as balloon-assisted self-expansion can also be utilized.

The integrated embolic protection element 305 is retracted and withdrawn with the sheath 300 after the diagnostic or interventional procedure has been completed. The sheath 300 may include features that facilitate retraction of the integrated embolic protection element 305 as shown in FIG. 3D. The upstream or distal end of the embolic protection element 305 may be coupled to one or more tethers 350 which may form a circumferential loop therearound. Similar to the tethers 195 described above, the tethers 350 can be retracted to close the upstream or distal end of the embolic protection element 305 prior to retraction of the sheath 300. The tethers 350 may also be coupled to other sections of the embolic protection element to facilitate closure of the embolic protection element 305 or retraction thereof. In some embodiments, a pull loop or other graspable structure near the downstream or proximal end of the embolic protection element 305 may be connected to the retraction members or tethers 350 by one or more connecting members.

Also, the sheath 300 may further comprise a conical guiding structure 360 which at the upstream or distal end be coupled to the cylindrical outer structure 320 and/or the stent-like support structure 345. At the downstream or proximal end, the conical guiding structure 360 is coupled to the outer portion of the main tubular body of the sheath 300 with a sliding mechanism 300. The conical guiding structure 360 may be similar to the conical guiding structure 185 described above, and may facilitate the collapse of embolic protection element 305 when the larger diameter tube 330 is advanced thereover.

As shown in FIG. 3D, the porous mesh material 306 may comprise one or more side ports 370 similar to the side ports 161 through which a second catheter or other interventional device may be passed through to access a surgical site. The side port 370 may be collapsible and closeable so that no emboli passed through the side port 370 when it is not being used. Alternatively, the porous mesh material 306 and the stent-like support structure 345 may be resilient enough so that a second catheter or other interventional device may be passed through its pores to access a surgical site without permanently affecting the pore sizes of the aforementioned structures.

The embolic protection element 305 may be constructed with the porous mesh material 306 and the stent-like support structure 345 having approximately the relative longitudinal dimensions shown in 3D. Alternatively, the porous mesh material 306 and the stent-like support structure 345 can each be made longer or shorter without adversely affecting the performance of the embolic protection element 305. In alternative embodiments, the stent-like support structure 345 can be made slightly conical with the larger end of the cone on the upstream or proximal side.

The entire embolic protection element 305 or a portion of it may be coated with an anti-thrombogenic coating, for example, a bonded heparin coating, to reduce the formation of clots that could become potential emboli. Alternatively or in addition, the embolic protection device 305 or a portion of it may have a drug-eluting coating containing an anti-inflammatory or antistenosis agent. The embolic protection element 305 can also be used for embolic protection of other organ systems. For example, the embolic protection element 305 can be deployed in the patient's descending aorta for preventing embolic particles in the aortic blood flow from entering the renal arteries and embolizing in the patient's kidneys. Alternatively or in addition, the entire sheath 300 or portions of it may be radiopaque to facilitate viewing of the sheath 300 as a procedure proceeds. Radiopaque markers may also be coupled to one or more portions of the sheath 300.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for introducing a catheter through an access sheath having integrated embolic protection, said method comprising:
   positioning the access sheath in a blood vessel with an open distal end of the access sheath directed against the direction of blood flow;
   deploying an embolic filter about the open distal end of the access sheath, wherein a cylindrical outer portion of the embolic filter contacts a wall of the blood vessel and a conical inner portion defines a collection chamber between an inner surface of the cylindrical outer portion and an outer surface of the conical inner portion, wherein the conical inner portion is oriented to collect emboli in the blood in the collection chamber; and
   introducing a catheter through a lumen of the access sheath while the embolic filter remains deployed about the open distal end of the access sheath.

2. A method as in claim 1, wherein the access sheath is positioned through a tubular outer delivery sheath that maintains the embolic filter in an undeployed retracted condition when the embolic filter is therewithin, and wherein the embolic filter deploys into the deployed expanded configuration when the embolic filter is advanced out of the tubular outer delivery sheath.

3. A method as in claim 1, wherein the blood vessel is the aorta.

4. A method as in claim 3, wherein the cylindrical outer portion of the embolic filter covers the ostia of the cerebral arteries of the aortic arch.

5. A method as in claim 1, wherein a distal end of the conical inner portion of the filter is fixedly attached to the open distal end of the access sheath and a distal end of the cylindrical outer portion of the filter is open and free of attachment to the access sheath.

6. A method as in claim 5, the conical inner portion is positioned inside the cylindrical outer portion and has a wider proximal end joined to the cylindrical outer portion.

7. A method as in claim 6, wherein a distal end of the embolic filter is open for blood to flow between the conical inner portion and the cylindrical outer portion, with a space between the conical inner portion and the cylindrical outer portion defining the collection chamber for captured emboli.

8. A method as in claim 1, further comprising deploying a stent-like support scaffold about the cylindrical outer portion of the filter for supporting the cylindrical outer portion.

9. A method as in claim 1, wherein the deploying the embolic filter comprises releasing the embolic filter from constraint to allow the embolic filter to self-expand.

10. A method as in claim 1, further comprising pulling on a graspable structure to close the distal end of the cylindrical outer portion and seal the collection chamber.

11. A method as in claim 10, further comprising withdrawing the filter from the blood vessel after the distal end of the cylindrical outer portion has been closed.

12. A method as in claim 1, further comprising introducing a second catheter, guide-wire, delivery sheath, or other surgical tool through a closeable access port in the filter.

13. A method as in claim 1, further comprising performing at least one of a valve replacement, balloon valvuloplasty, and blood vessel ablation with the catheter that has been introduced.

14. A method for introducing a catheter through an access sheath having integrated embolic protection, said method comprising:
   positioning the access sheath in a blood vessel with an open distal end of the access sheath directed against the direction of blood flow;
   deploying an embolic filter about the open distal end of the access sheath, wherein a cylindrical outer portion of the embolic filter contacts a wall of the blood vessel and a conical inner portion defines a collection chamber between an inner surface of the cylindrical outer portion and an outer surface of the conical inner portion, wherein the conical inner portion is oriented to collect emboli in the blood in the collection chamber; and
   introducing a catheter through a lumen of the access sheath while the embolic filter remains deployed about the open distal end of the access sheath; and
   wherein a distal end of the conical inner portion of the filter is fixedly attached to the open distal end of the access sheath and a distal end of the cylindrical outer portion of the filter is open and free of attachment to the access sheath.

15. A method as in claim 14, the conical inner portion is positioned inside the cylindrical outer portion and has a wider proximal end joined to the cylindrical outer portion.

16. A method as in claim 15, wherein a distal end of the embolic filter is open for blood to flow between the conical inner portion and the cylindrical outer portion, with a space between the conical inner portion and the cylindrical outer portion defining the collection chamber for captured emboli.

* * * * *